United States Patent [19]

Shinmen et al.

[11] Patent Number: 5,401,646
[45] Date of Patent: Mar. 28, 1995

[54] PROCESS FOR PRODUCTION OF BISHOMO-GAMMA-LINOLENIC ACID AND EICOSAPENTAENOIC ACID

[75] Inventors: Yoshifumi Shinmen; Hideaki Yamada; Sakayu Shimizu, all of Kyoto, Japan

[73] Assignee: Suntory Limited, Osaka, Japan

[21] Appl. No.: 106,637

[22] Filed: Aug. 16, 1993

Related U.S. Application Data

[63] Continuation of Ser. No. 657,630, Feb. 21, 1991, abandoned, which is a continuation of Ser. No. 71,039, Jul. 8, 1987, abandoned.

[30] Foreign Application Priority Data

Jul. 8, 1986 [JP] Japan .................................. 61-158650
Jul. 8, 1986 [JP] Japan .................................. 61-158651

[51] Int. Cl.$^6$ ................ C12P 7/64; C12P 7/62; C12N 1/14
[52] U.S. Cl. .................... 435/134; 435/135; 435/911; 435/244; 435/171; 435/254.1
[58] Field of Search ........... 435/134, 135, 911, 171, 435/244, 254.1

[56] References Cited

U.S. PATENT DOCUMENTS 4,485,173 11/1984 Gierhart .............................. 435/134

FOREIGN PATENT DOCUMENTS

| | | |
|---|---|---|
| 0125764 | 11/1984 | European Pat. Off. .......... 435/134 |
| 0155420 | 9/1985 | European Pat. Off. .......... 435/134 |
| WO8603518 | 6/1986 | European Pat. Off. ........ C12P 7/64 |
| 0223960 | 6/1987 | European Pat. Off. .......... 435/134 |
| 60-168391 | 8/1985 | Japan ............................ C12P 7/64 |
| 60-259192 | 12/1985 | Japan ............................ C12P 7/64 |

OTHER PUBLICATIONS

Gams, "A Key to the Species of Mortierella", *Persoonia*, vol. 9, Part 3 (1977), pp. 381–391.

Shinmen, et al., "Production of arachidonic acid by Mortierella fungi", *Appl. Microbiol. Biotechnol.*, vol. 31 (1989), pp. 11–16.

Haskins et al, "Steroids And The Stimulation Of Sexual Reproduction Of A Species Of Pythium", *Canadian Journal of Microbiology*, vol. 10, pp. 187–195 (1964).

Chemical Abstracts, vol. 101, No. 19, 5th Nov. 1984, p. 539, No. 169107e, Columbus, Ohio.

Chemical Abstracts, vol. 98, No. 5, 31st Jan. 1983, p. 537, No. 33069f, Columbus, Ohio.

*Primary Examiner*—Irene Marx
*Attorney, Agent, or Firm*—Burns, Doane, Swecker & Mathis

[57] ABSTRACT

A process for the production of a fatty acid selected from the group consisting of bishomo-γ-linolenic acid and eicosapentaenoic acid comprising the steps of culturing a microorganism belonging to the genus Mortierella and capable of producing at least one of the fatty acids to obtain a cultured product, and recovering at least one of the fatty acids; and a process for the production of lipid containing such fatty acids.

8 Claims, No Drawings

PROCESS FOR PRODUCTION OF BISHOMO-GAMMA-LINOLENIC ACID AND EICOSAPENTAENOIC ACID

This application is a continuation of application Ser. No. 07/657,630, filed Feb. 21, 1991, now abandoned, in turn a continuation of Ser. No. 07/071,039, filed Jul. 8, 1987, now abandoned.

BACKGROUND OF THE INVENTION

1. Field of the Invention

The present invention relates to a new process for the production of bishomo-γ-linolenic acid and eicosapentaenoic acid.

2. Description of the Related Art

It is known that bishomo-γ-linolenic acid and eicosapentaenoic acid are present in and can be extracted from fish oils and seaweeds or algae. However, the production process is disadvantageous in that the content of such acids in fish oils is very low, insufficient purification of the products leads to products having a fish-oil odor, and culturing of the algae is difficult. Therefore, there is a strong demand for a process for the production of bishomo-γ-linolenic acid and eicosapentaenoic acid whereby such acids can be easily and industrially produced at a low cost.

In this connection, a process for the production of bishomo-γ-linolenic acid using microorganisms, and a process for the production of eicosapentaenoic acid using a microorganism belonging to the genus Mortierella, have not been hitherto considered.

These processes, however, have the disadvantages of a low yield, long term fermentation, and a complicated production process.

SUMMARY OF THE INVENTION

Accordingly, the present invention provides a new process for the production of a fatty acid selected from the group consisting of bishomo-γ-linolenic acid and eicosapentaenoic acid, comprising the steps of:
culturing a microorganism belonging to the genus Mortierella and capable of producing at least one of said fatty acids to obtain a cultured product; and recovering at least one of said fatty acids.

Moreover, the present invention provides a process for the production of a lipid containing at least one fatty acid selected from the group consisting of bishomo-γ-linolenic acid and eicosapentaenoic acid, comprising the steps of:
culturing a microorganism belonging to the genus Mortierella and capable of producing at least one of said fatty acids to obtain a culture product;
separating the cultured product to microbial cells and a supernatant;
extracting the separated cultured product selected from the group of the microbial cells and the supernatant with an extraction agent to obtain an extract; and
eliminating the extraction agent from the extract to obtain the lipid.

DESCRIPTION OF THE PREFERRED EMBODIMENT

In the present invention, as a producer microorganism, any strain belonging to the genus Mortierella capable of producing bishomo-γ-linolenic acid and/or eicosapentaenoic acid can be used. For example, *Mortierella elongata* IFO 8570, *Mortierella exigua* IFO 8571, and *Mortierella hygrophila* IFO 5941 can be used. These strains are stored in the Osaka Institute for Fermentation; 17–85, Juso-honmachi 2-chome, Yodogawa-ku, Osaka 532, Japan, and are available to the public without limitation.

Moreover, a new strain *Mortierella elongata* SAM 0219 can be used. This strain was newly isolated from soil and identified by the present inventors, and was deposited with the Fermentation Research Institute, Agency of Industrial Science and Technology (FRI), Higashi 1-1-3, Yatabe-cho, Tsukuba-gun, Ibaraki-ken, Japan as FERM P-8703 on Mar. 19, 1986, and transferred to International Deposition under the Budapest Treaty as FERM BP-1239 on Dec. 22, 1986.

The above-mentioned new strain SAM 0219 (FERM BP-1239) has the following taxonomical properties:

Cultural characteristics on various culture media

Culture condition: 25° C. in the dark

1. Malt extract agar medium

Colonies grow fast, attaining a diameter of 28 to 31 mm in two days and a diameter of 65 to 72 mm in five days; colonies are lobed; the formation of aerial mycelium is scanty; sporulation is good; sporangiophores arise from the aerial hyphae; the mycelium has a garlic-like odor.

2. Potato dextrose agar medium

Colonies grow fast, attaining a diameter of 27 to 31 mm in two days and a diameter of 75 to 80 mm in five days; colonies form a rosette pattern of dense lobes; much aerial mycelium is formed at the center of the colony; the reverse side of the colony is yellowish white or yellow in color; sporulation is poor; the mycelium has a rather strong garlic-like odor.

3. Czapek's agar medium

Colonies grow moderately fast, attaining a diameter of 22 to 24 mm in two days and a diameter of 50 to 53 mm in five days; the formation of aerial mycelium is scanty; occasionally, the aerial hyphae cling tightly to each other; sporulation is abundant; the mycelium has a garlic-like odor.

4. LCA agar medium (prepared according to Koichiro Miura and Mitsuyo Y. Kudo, "An agar-medium for aquatic Hyphomycetes" Transactions of the Mycological Society of Japan vol. 11, p 116–118, 1970)

Colonies grow fast, attaining a diameter of 27–29 mm in two days and a diameter of 64 to 66 mm in five days; colonies are lobed; the formation of aerial mycelium is scanty, except at the center of the colony; sporulation is good; sporangiophores arise from the aerial hyphae; the mycelium has a garlic-like odor.

Microscopic Examination

Sporangiophore, mode of branching sporangiophore, sporangium, sporangiospore, etc., were microscopically observed for microscopic preparates and the colony per se. from various media.

A sporangiophore is tapered and has a length of 87.5 to 320 μm, a width of 3 to 7.5 μm at the root, and a width of 1.0 to 2.5 μm at the top, and often branches at the root. A sporangium is spherical in form, has a diameter of 15 to 30 μm, contains many ascospores therein, and has an unclear color after the detaching of the sporangiospore. A sporangiospore is elliptical or, rarely, renal in form, has a smooth surface, and a size of 7.5 to 12.5×5 to 7.5 μm. A relatively large number of chlamydospores are formed. Chlamydosphores are present separately or, rarely, linked in a chain form. Occasionally, several mycelia appear from the edge of the chlamydosphore. The chlamydosphore is elliptical or subspherical in form, and has a size of 12.5 to 30×7.5 to 15 μm, or a diameter of 12.5 to 15 μm. Zygospores are not observed.

Physiological Properties

Optical growth condition:
pH: 6 to 9,
Temperature: 20° C. to 30° C.;
Range for growth:
pH: 4 to 10,
Temperature: 5° C. to 40° C.

On the basis of the above-mentioned taxonomical properties, and according to J. A. von Arx, "The Genera of Fungi Sporulating in Pure Culture" 3rd ed., J. Cramer, 1981; and K. H. Domsch, W. Gams and T. H. Anderson, "Compendium of Soil Fungi" Academic Press, 1980, the strain SAM-0219 of the present invention is considered to be a fungus belonging to the genus Mortierella, because a sporangium is formed at a top of a sporangiophore, the sporangium has no collumella, the sporangiospore has no appendage, and the mycelium has a garlic-like odor.

Therefore, the taxonomical properties of the strain of the present invention were compared with those of known species of the genus Mortierella according to W. Gams, "A key to the species of Mortierella, Persoonia 9: p 381–391, 1977. As a result, because the colony is not velvety, the mycelium has a garlic-like odor, a sporangiophore has a length of 87.5 to 320 μm and branches at only its lower part and does not branch racemosely, and a sporangium contains many sporangiospore therein, the strain in question was considered to fall under the genus Mortierella, subgenus Mortierella, section Hygrophila. The section Hygrophila includes 22 species. According to the comparison of the present strain with these 22 species, the present strain is similar to *Mortierella zychae, M. elongatula,* and *M. elongata.*

Therefore, the strain of the present invention was compared with the above-mentioned three strains, referring to K. H. Domsch, W. Gams, and T.-H. Anderson, "Compendium of Soil Fungi", Academic Press, 1980; W. Gams, Some New or Noteworthy Species of Mortierella"; Persoonia 9: 111–140, 1976; G. Linnemann, "Mortierella Coemans 1863"; H. Zyche and R. Siepmann, "Mucorales Eine Beschreibung Aller Gattungen und Arten dieser Pilzgruppe", p 155–241, J. Cramer, 1965. The present strain is clearly different from *M. zychae* in the length and width of the sporangiophore at the base, and the size of the sporangium. Moreover, the present strain is different from *M. elongatula* in the shape and size of the sporangiosphore. The present strain is different from *M. elongata* in that sporangiophore is rather shorter, the chlamydosphore is ellipsoidal or subglobose in form, chlamydospores are rarely linked to each other in a chain form, and a small number of radiating hyphae exist. However, the present inventors concluded that such differences between the present strain and *M. elongata* are not sufficient to distinguish the present strain from *M. elongata,* and thus identified the strain of the present invention as *Mortierella elongata,* and designated it as strain SAM 0219.

Spores, mycelia, or a preculture is used as an inoculum for culturing the present strains. The medium used may be a liquid or solid medium. A liquid medium contains as a carbon source, for example, glucose, fructose, xylose, saccharose, maltose, soluble starch, molasses, glycerol, or mannitol. Nitrogen sources include organic substances such as peptones, yeast extract, meat extract, casamino acid, corn steep liquor, and inorganic substances such as sodium nitrate, ammonium nitrate, ammonium sulfate, and the like. If necessary, inorganic salts such as phosphate salts, magnesium sulfate, ferrous sulfate and cupric sulfate, and vitamins may be included in a medium. The concentration of these components is selected so that such components do not adversely affect the growth of the microorganism used. Practically, the concentration of the carbon source is 0.1 to 30% by weight, preferably 1 to 10% by weight, relative to the total weight of the medium. The concentration of the nitrogen source is 0.01 to 5% by weight, preferably 0.1 to 2% by weight, relative to the total weight of the medium.

To enhance the production of target fatty acids, in addition to the above-mentioned medium components, hydrocarbons, fatty acids or salts thereof, or fats, are preferably added to a medium in an amount of 0.01% to 20%. Hydrocarbons are preferably added to a medium at the start of culturing, and fatty acids or salts thereof, or fats, are preferably added at the start of and/or during culturing. When such an additive is used during culturing, it is added at one time, stepwise, or continuously.

The culturing temperature ranges 5° C. to 40° C. For the production of bishomo-γ-linolenic acid, the culturing temperature is preferably 20° C. to 30° C. For the production of eicosapentaenoic acid, the culturing temperature is preferably 10° C. to 20° C. from the start to the end of the culturing. Alternatively, the culturing is carried out at a temperature between 20° C. and 30° C. until microbial cells have a sufficient growth, and the temperature is then changed to a temperature between 10° C. and 20° C. to produce eicosapentaenoic acid. This temperature control, can increase a ratio of eicosapentaenoic acid in relation to total fatty acids produced. A pH value of the medium is 4 to 10, preferably 6 to 9.

Culturing is preferably carried out with aeration and/or agitation, with shaking in a liquid medium, or with standing, and is usually carried out for 2 to 10 days.

When culturing is carried out on a solid medium, the solid medium is composed of wheat bran, chaff or rice bran supplemented with water in an amount of 50 to 100% by weight relative to the wheat bran, chaff or rice bran. If necessary, the medium is supplemented with a small amount of nitrogen source, inorganic salts, and/or minor nutrients. Culturing is carried out at a temperature of 5° C. to 40° C., preferably 20° C. to 30° C., for 3 to 14 days.

During culturing, lipids containing target fatty acids are mainly intracellularly accumulated. When a liquid medium is used, target fatty acids are recovered from the cultured cells by the following procedure.

After culturing, cultured cells are collected from the cultured broth by a conventional means such as filtration or centrifugation, the cells are washed with water, and preferably, the washed cells are dried. Drying is carried out by, for example, lyophilization or air-drying. The dried cells are treated with an organic solvent or a mixture thereof, preferably under a nitrogen stream, to extract a lipid containing target fatty acids. The organic solvent or mixture thereof is, for example, ethers such as ethyl ether, hydrocarbons such as hexane, alcohols such as methanol or ethanol, halo-hydrocarbon such as chloroform or dichloromethane, petroleum ether, as well as a mixture of chloroform, methanol and water, or a combination of methanol and petroleum ether alternately used. By distilling off the solvent, a lipid containing concentrated target fatty acids is obtained.

Alternatively, wet cells can be subjected to extraction. In such a case, a water-miscible solvent such as methanol or ethanol, or a water-miscible solvent comprising the water-miscible solvent and water or other organic solvent is used. The extraction procedure is the same as described for dried cells.

The lipid thus obtained contains target fatty acids in the form of a lipid compound such as fat. Although the target fatty acids can be isolated in the form of a free acids, they are preferably isolated in the form of an ester with a lower alcohol, for example, as methyl esters. By converting target fatty acids to such esters, each is easily separated from other lipid components, and from another target fatty acid and other fatty acids formed during culturing, such as palmitic acid, oleic acid, linoleic acid and the like, which are also esterified at the same time as the target fatty acids are esterified. To obtain methyl esters of the target fatty acids, for example, the lipid prepared as described above is treated with a 5 to 10% hydrochloric acid solution in absolute methanol or a 10 to 50% $BF_3$ solution in methanol for 1 to 24 hours at room temperature.

The mixture thus obtained is extracted with an organic solvent such as hexane, ethyl ether or ethyl acetate, to recover methyl ester of the target fatty acids. Next, the extract is dried over anhydrous sodium sulfate, and the solvent is distilled under reduced pressure to obtain a residue mainly comprising a fatty acid mixture. The mixture contains, in addition to the target compounds, methyl arachidonate, methyl palmitate, methyl stearate, methyl oleate and the like. From the mixture, methyl bishomo-γ-linolenate and methyl eicosapentaenoate are separately isolated by column chromatography, low temperature crystallization, urea-adducting method, or a combination thereof.

The isolated methyl ester of a target fatty acid is then hydrolyzed with an alkali and extracted with an organic solvent such as ethyl ether, ethyl acetate, or the like to obtain the target fatty acid in a free form.

Alternatively, a target fatty acid can be obtained, without conversion to methyl ester, by alkalolysis with, for example, 5% sodium hydroxide at a room temperature for 2 to 3 hours, followed by extraction of the fatty acids from the alkalolysis product and isolation of the target fatty acid.

EXAMPLES

The present invention will now be further illustrated by, but is by no means limited to, the following examples.

EXAMPLE 1

(Production of bishomo-γ-linolenic acid)

50 ml of a medium containing 5% glucose, 0.5% peptone, 0.3% yeast extract and 0.3% malt extract (pH 6.0) was prepared and charged into a 500 ml-volume Sakaguchi flask, and the whole was autoclaved for 20 minutes at 120° C. After cooling, *Mortierella elongata* SAM 0219 (FERM BP-1239) was inoculated into the medium, and then cultured for 5 days at 28° C. with reciprocal shaking at 110 rpm. After culturing, the cultured broth was filtered to recover cells. The cells were then completely washed with water and lyophilized to obtain 1.2 g of dried cells. The cells were extracted with a mixture of chloroform, methanol, and water, according to Bligh and Dyer's one phase extraction method, to obtain 290 mg of whole lipid. The lipid was treated with a mixture of methanol and hydrochloric acid (95:5) at 20° C. for three hours to esterify the arachidonic acid. The reaction mixture was extracted with ethyl ether to obtain 180 mg of a mixture of fatty acid methyl esters. The mixture was separated by column chromatography using octa decylsilane with elution by 95% acetonitrile solution to obtain fractions containing methyl bishomo-γ-linolenate. After the fractions were combined, the solvent was distilled off on a rotary evaporator to obtain 5.2 mg of purified methyl bishomo-γ-linolenate. The methyl bishomo-γ-linolenate preparation thus obtained was compared with a methyl bishomo-γ-linolenate prepared from a commercially available bishomo-γ-linolenic acid, by gas chromatography, high performance liquid chromatography, and mass spectrometry. Both preparations showed the same results, revealing that the preparation prepared in this Example is in fact methyl bishomo-γ-linolenate. The amount of methyl bishomo linolenate before and after the purification per cultured broth was 0.18 mg/ml and 0.10 mg/ml respectively; and those per dried cells were 7.5 mg/g and 4.3 mg/g respectively.

EXAMPLE 2

(Production of bishomo-γ-linolenic acid)

5 l of a medium having the same composition as described in Example 1 was charged in a 15 l-volume jar fermenter, and the medium was sterilized at 120° C. for 40 minutes. After cooling, the fermenter was inoculated with 200 ml of a preculture of *Mortierella elongata* SAM 0219 (FERM BP-1239). Culturing was carried out at 30° C. for 3 days with aeration of 0.5 v.v.m. The cultured broth was then filtered to obtain 370 g of wet cells and 4050 l of a filtrate. The cells were dried to obtain 120 g of dried cells. The dried cells thus obtained were subjected to extraction, hydrolysis and methyl-esterification according to the same procedures as described in Example 1, to obtain 31 g of whole lipid containing 19 g of a mixture of fatty acid methyl esters. The amount of methyl bishomo-γ-linolenate formed was 0.19 g/l broth, and 7.9 mg/g dried cells.

On the other hand, 4,050 ml of the above-mentioned filtrate was subjected to extraction, hydrolysis and methyl-esterification to obtain 172 mg of a mixture of fatty acid methyl esters including 5% by weight of methyl bishomo-γ-linolenate relative to a weight of the mixture.

EXAMPLE 3

(Production of bishomo-γ-linolenic acid)

The same procedure as described in Example 1 was carried out except that *Mortierella exigua* IFO 8571, and *Mortierella hygrophila* IFO 5941 were used. 65 mg and 93 mg of mixtures of fatty acid methyl esters were obtained respectively, and from these mixtures, 2.7 mg and 4.5 mg of methyl bishomo-γ-linolenate was isolated and purified, respectively.

EXAMPLE 4

(Production of bishomo-γ-linolenic acid)

20 ml of a medium containing 2% glucose, 1% yeast extract, and 0.2% Tween 20, as well as an additive, i.e., 0.5% of a different kind of hydrocarbons, sodium salt of fatty acid or lipid listed in the following Table 1 (pH 6.0) was charged in each 100 ml-volume Erlenmeyer flask, and the flasks were autoclaved at 120° C. for 20 minutes. *Mortierella elongata* SAM 0219 (FERM BP-1239) were inoculated into the medium and then cultured for 5 days at 28° C. with rotary shaking at 200 rpm. The cultured broths were separately filtered to obtain cells. The cells were then subjected to extraction, hydrolysis, and methyl-esterification according to the same procedure as described in Example 1. The weight of the dried cells, amount of whole lipid, amount of whole fatty acid methyl ester, content of methyl arachidonate, and amount of methyl arachidonate per cultured broth are set forth for each additive.

TABLE 1

| Additive | Weight of dried cells (mg) | Amount of whole lipid (mg) | Amount of whole fatty acid methyl esters (mg) | Content of methyl bishomo-γ-linolenate (%) | Amount of methyl bishomo-γ-linolenate per broth (mg/ml) |
| --- | --- | --- | --- | --- | --- |
| Octadecane | 330 | 82 | 75 | 5.0 | 0.19 |
| Sodium oleate | 310 | 80 | 74 | 5.1 | 0.19 |
| Sodium linoleate | 320 | 83 | 73 | 5.9 | 0.22 |
| Olive oil | 390 | 95 | 82 | 5.8 | 0.24 |
| Cotton seed oil | 410 | 105 | 91 | 6.0 | 0.27 |
| Coconut oil | 370 | 91 | 84 | 5.5 | 0.23 |
| No addition | 1200 | 290 | 180 | 5.0 | 0.18 |

As seen from the Table 1, the addition of hydrocarbons, salts of fatty acids and lipid increased the production of bishomo-γ-linolenic acid by 2 to 20% relative to the no-addition control.

EXAMPLE 5

(Production of bishomo-γ-linolenic acid)

20 ml of medium containing 2% glucose and 1% yeast extract was charged in 100 ml-volume Erlenmeyer flasks, and the flasks were autoclaved at 120° C. for 20 minutes. *Mortierella elongata* SAM 0219 (FERM BP-1239) was inoculated into the medium, and then incubated at 28° C. for 4 days. After the addition of 100 mg of a different kind of sodium salt of fatty acid or lipid into each flask, incubation was continued at 28° C. for an additional 2 days. The cultures were separately filtered to obtain cells, and the cells were then subjected to extraction, hydrolysis, and methyl-esterification according to the same procedure as described in Example 1. The amount of methyl bishomo-γ-linolenate per dried cells and per cultured broth was as set forth for each additive in Table 2.

TABLE 2

| Additive | Amount of methyl bishomo-γ-linolenate | |
| --- | --- | --- |
| | mg/g dried cells | mg/ml broth |
| Sodium stearate | 9 | 0.14 |
| Sodium oleate | 10 | 0.17 |
| Sodium linoleate | 11 | 0.19 |
| Sodium linolenate | 12 | 0.17 |
| Olive oil | 9 | 0.20 |

TABLE 2-continued

| Additive | Amount of methyl bishomo-γ-linolenate | |
| --- | --- | --- |
| | mg/g dried cells | mg/ml broth |
| Soybean oil | 10 | 0.22 |
| Linseed oil | 10 | 0.19 |
| No addition | 8 | 0.12 |

As seen from Table 2, the addition of salts of fatty acids and lipids at the fourth day of culturing increased the production of bishomo-γ-linolenic acid by 10 to 80% relative to the no-addition control.

EXAMPLE 6

(Production of eicosapentaenoic acid)

50 ml of a medium containing 5% glucose, 0.5% peptone, 0.3% yeast extract and 0.3% malt extract (pH 6.0) was prepared and charged into a 500 ml-volume Sakaguchi flask, and the whole was autoclaved for 20 minutes at 120° C. After cooling, *Mortierella elongata* SAM 0219 (FERMBP-1239) was inoculated into the medium, and then cultured for 5 days at 28° C. with reciprocal shaking at 110 rpm. After culturing, the cultured broth was filtered to recover cells. The cells were then completely washed with water and lyophilized to obtain 0.7 g of dried cells. The cells were extracted with a mixture of chloroform, methanol, and water, according to Bligh and Dyer's one phase extraction method, to obtain 150 mg of a whole lipid. The lipid was treated with a mixture of methanol and hydrochloric acid (95:5) at 20° C. for three hours to esterify the arachidonic acid. The reaction mixture was extracted with ethyl ether to obtain 95 mg of a mixture of fatty acid methyl esters. The mixture contained 12% methyl palmitate, 12% methyl stearate, 24% methyl oleate, 5% methyl linoleate, 8% methyl γ-linolenate, 10% methyl arachidonate, 5% methyl bishomo-γ-linolenate, and 13% methyl eicosapentaenoate and 17% other components, as determined by gas chromatography. The mixture was separated by column chromatography using octa decylsilane with elution by 95% acetonitrile solution to obtain fractions containing methyl eicosapentaenoate. After the fractions were combined, the solvent was distilled off on a rotary evaporator to obtain 6.5 mg of purified methyl eicosapentaenoate. The methyl eicosapentaenoate preparation thus obtained was compared with a commercially available authentic methyl eicosapentaenoate preparation, by gas chromatography, high performance liquid chromatography, and mass spectrometry. Both preparations showed the same results, revealing that the preparation prepared in this Example is in fact methyl eicosapentaenoate. The amount of methyl eicosapentaenoate before and after purification per cultured broth was 0.25 mg/ml and 0.13 mg/ml respectively; and those per dried cells were 18 mg/g and 9 mg/g respectively.

According to the same procedure as described above for methyl eicosapentaenoate, from the above-mentioned mixture of fatty acid methyl esters, methyl bishomo-γ-linolenate can be obtained.

Moreover, by hydrolyzing the methyl eicosapentaenoate and methyl bishomo-γ-linolenate, eicosapentaenoic acid and bishomo-γ-linolenic acid can be obtained respectively.

EXAMPLE 7

(Production of eicosapentaenoic acid)

5 l of a medium having the same composition as described in Example 1 was charged in a 15 l-volume jar fermenter, and the medium was sterilized at 120° C. for 40 minutes. After cooling, the fermenter was inoculated with 200 ml of a preculture of *Mortierella elongata* SAM 0219 (FERM BP-1239). Culturing was carried out at 30° C. for 3 days with aeration of 0.5 v.v.m. The cultured broth was then filtered to obtain 150 g of wet cells and 4270 l of a filtrate. The cells were dried to obtain 50 g of dried cells. The dried cells thus obtained were subjected to extraction, hydrolysis and methyl-esterification according to the same procedures as described in Example 6, to obtain 18 g of whole lipid containing 8 g of a mixture of fatty acid methyl esters. The mixture contained 13% methyl palmitate, 14% methyl stearate, 28% methyl oleate, 8% methyl linoleate, 8% methyl γ-linolenate, 13% methyl arachidonate, 8% methyl bishomo-γ-linolenate, 6% methyl eicosapentaenoate, and 17% other components, as determined by the same procedure as described in Example 6. The amount of methyl eicosapentaenoate formed was 0.11 g/l broth, and 9.6 mg/g dried cells.

On the other hand, 4,270 ml of the above-mentioned filtrate was subjected to extraction, hydrolysis and methyl-esterification to obtain 82 mg of a mixture of fatty acid methyl esters including 7% by weight of methyl eicosapentaenoate relative to a weight of the mixture.

Bishomo-γ-linolenate can be obtained by the same procedure as described above for methyl eicosapentaenoate, from the above-mentioned mixture of fatty acid methyl esters.

Moreover, eicosapentaenoic acid and bishomo-γ-linolenic acid can be obtained by hydrolyzing the methyl eicosapentaenoate and bishomo-γ-linolenate.

EXAMPLE 8

(Production of eicosapentaenoate)

The same procedure as described in Example 6 was carried out except that *Mortierella exigua* IFO 8571, and *Mortierella hygrophila* IFO 5941 were used. 47 mg and 72 mg of mixtures of fatty acid methyl esters were obtained respectively, and from these mixtures, 12 mg and 20 mg of methyl eicosapentaenoate was isolated and purified, respectively.

EXAMPLE 9

(Production of eicosapentaenoate)

20 ml of a medium containing 2% glucose, 1% yeast extract, and 0.2% Tween 20, as well as an additive, i.e., 0.5% of a different kind of hydrocarbons, sodium salt of fatty acid or lipid listed in the following Table 1 (pH 6.0) was charged in each 100 ml-volume Erlenmeyer flask, and the flasks were autoclaved at 120° C. for 20 minutes. *Mortierella elongata* SAM 0219 (FERM BP-1239) were inoculated the medium and then cultured for 5 days at 28° C. with rotary shaking at 200 rpm. The cultured broths were separately filtrated to obtain cells. The cells were then subjected to extraction, hydrolysis, and methyl-esterification according to the same procedure as described in Example 6. The weight of the dried cells, amount of whole lipid, amount of whole fatty acid methyl ester, content of methyl eicosapentaenoate, and amount of methyl eicosapentaenoate per cultured broth are set forth for each additive.

TABLE 3

| Additive | Weight of dried cells (mg) | Amount of whole lipid (mg) | Amount of whole fatty acid methyl esters (mg) | Content of methyl eicosapentaenoate (%) | Amount of methyl eicosapentaenoate per broth (mg/ml) |
|---|---|---|---|---|---|
| Hexadecane | 310 | 80 | 73 | 0.50 | 0.018 |
| Octadecane | 330 | 84 | 74 | 0.32 | 0.012 |
| Sodium oleate | 290 | 78 | 70 | 0.41 | 0.014 |
| Sodium linoleate | 300 | 81 | 69 | 9.2 | 0.32 |
| Olive oil | 380 | 92 | 79 | 0.63 | 0.024 |
| Coconut oil | 390 | 95 | 82 | 1.2 | 0.049 |
| Linseed oil | 370 | 90 | 80 | 11 | 0.44 |
| No addition | (Not detectable) | | | | |

As seen from Table 3, the addition of linseed oil or sodium linoleate increased the amount of eicosapentaenoic acid produced to 0.44 mg and 0.32 mg/ml medium respectively. Also, the addition of hydrocarbons, salts of fatty acid or lipid remarkably increased the production of eicosapentanoic acid, but the no-addition control provided no detectable fatty acids.

EXAMPLE 10

(Production of eicosapentaenoic acid)

20 ml of a medium containing 2% glucose and 1% yeast extract was charged in 100 ml-volume Erlenmeyer flasks, and the flasks were autoclaved at 120° C. for 20 minutes. *Mortierella elongata* SAM 0219 (FERM BP-1239) was inoculated the medium, and the incubated at 28° C. for 5 days, and then 12° C. for 4 days. The culture was filtered to obtain cells. The cells were then subjected to extraction, hydrolysis, and methyl-esterification according to the same procedure as described in Example 6. 75 mg of a mixture of fatty acid methyl esters containing 9% methyl eicosapentaenoate was obtained.

EXAMPLE 11

(Production of eicosapentaenoate)

20 ml of a medium containing 2% glucose and 1% yeast extract was charged in 100 ml-volume Erlenmeyer flasks, and the flasks were autoclaved at 120° C. for 20 minutes. *Mortierella elongata* SAM 0219 (FERM BP-1239) was inoculated the medium, and then incubated at 28° C. for 4 days. After the addition of 100 mg of a different kind of sodium salt of fatty acid or lipid into each flask, incubation was continued at 28° C. for an additional 2 days. The cultures were separately filtered to obtain cells. The cells were then subjected to extraction, hydrolysis, and methyl-esterification according to the same procedure as described in Example 6.

TABLE 4

| | Amount of methyl eicosapentaenoate | |
|---|---|---|
| Additive | mg/g dried cells | mg/ml broth |
| Sodium stearate | 0.4 | 0.006 |
| Sodium oleate | 0.6 | 0.010 |
| Sodium linoleate | 3 | 0.043 |
| Sodium linolenate | 3 | 0.047 |
| Olive oil | 0.1 | 0.003 |
| Soybean oil | 12 | 0.25 |

TABLE 4-continued

| Additive | Amount of methyl eicosapentaenoate | |
|---|---|---|
| | mg/g dried cells | mg/ml broth |
| Linseed oil | 10 | 0.19 |
| No addition | Not detectable | |

As seen from Table 4, the addition of salts of fatty acids and lipids at the fourth day of the culturing provided the production of 0.006 mg to 0.25 g/ml medium of eicosapentaenoic acid; while the no-addition control provided no detectable eicosapentaenoic acid.

We claim:

1. A process for producing bishomo-γ-linolenic acid, comprising the steps of:
    culturing in a nutrient medium containing an additive selected from the group consisting of a hydrocarbon, a fatty acid, a salt of a fatty acid, and a lipid, a microorganism selected from the group consisting of *Mortierella elongata* FERM BP-1239, *Mortierella exigua* IFO 8571, *Mortierella hygrophila* IFO 5941, and *Mortierella elongata* IFO 8570, to produce bishomo-γ-linolenic acid; and
    recovering the bishomo-γ-linolenic acid.

2. A process for producing bishomo-γ-linolenic acid, comprising the steps of:
    culturing in a nutrient medium a microorganism selected from the group consisting of *Mortierella elongata* FERM BP-1239, *Mortierella exigua* IFO 8571, *Mortierella hygrophila* IFO 5941, and *Mortierella elongata* IFO 8570;
    adding to said medium during culturing an additive selected from the group consisting of a fatty acid, a salt of fatty acid, and a lipid, to produce bishomo-γ-linolenic acid; and
    recovering the bishomo-γ-linolenic acid.

3. A process for producing a lipid containing bishomo-γ-linolenic acid, comprising the steps of:
    culturing in a nutrient medium containing an additive selected from the group consisting of a hydrocarbon, a fatty acid, a salt of a fatty acid, and a lipid, a microorganism selected from the group consisting of *Mortierella elongata* FERM BP-1239, *Mortierella exigua* IFO 8571, *Mortierella hygrophila* IFO 5941, and *Mortierella elongata* IFO 8570, to obtain a cultured broth;
    separating said cultured broth to obtain microbial cells and a supernatant;
    extracting said microbial cells with an extraction agent to obtain an extract; and
    eliminating the extraction agent from the extract to obtain the lipid containing bishomo-γ-linolenic acid.

4. A process for producing a lipid containing bishomo-γ-linolenic acid, comprising the steps of:
    culturing in a nutrient medium a microorganism selected from the group consisting of *Mortierella elongata* FERM BP-1239, *Mortierella exigua* IFO 8571, *Mortierella hygrophila* IFO 5941, and *Mortierella elongata* IFO 8570;
    adding to said medium during culturing an additive selected from the group consisting of a fatty acid, a salt of a fatty acid, and a lipid, to obtain a cultured broth;
    separating said cultured broth to obtain microbial cells and a supernatant;
    extracting said microbial cells with an extraction agent to obtain an extract; and
    eliminating the extraction agent from the extract to obtain the lipid containing bishomo-γ-linolenic acid.

5. A process for producing eicosapentaenoic acid, comprising the steps of:
    culturing in a nutrient medium containing an additive selected from the group consisting of a hydrocarbon, a fatty acid, a salt of a fatty acid, and a lipid, a microorganism selected from the group consisting of *Mortierella elongata* FERM BP-1239, *Mortierella exigua* IFO 8571, *Mortierella hygrophila* IFO 5941, and *Mortierella elongata* IFO 8570; and
    recovering eicosapentaenoic acid, wherein the culturing is carried out at a temperature between 10° C. and 20° C. for a sufficient period of time to produce eicosapentaenoic acid.

6. A process for producing eicosapentaenoic acid, comprising the steps of:
    culturing in a nutrient medium a microorganism selected from the group consisting of *Mortierella elongata* FERM BP-1239, *Mortierella exigua* IFO 8571, *Mortierella hygrophila* IFO 5941, and *Mortierella elongata* IFO 8570;
    adding to said medium during culturing an additive selected from the group consisting of a fatty acid, a salt of a fatty acid, and a lipid, to produce eicosapentaenoic acid; and
    recovering the eicosapentaenoic acid, wherein the culturing is carried out at a temperature between 10° C. and 20° C. for a sufficient period of time to produce eicosapentaenoic acid.

7. A process for producing a lipid containing eicosapentaenoic acid, comprising the steps of:
    culturing in a nutrient medium containing an additive selected from the group consisting of a hydrocarbon, a fatty acid, a salt of a fatty acid, and a lipid, a microorganism selected from the group consisting of *Mortierella elongata* FERM BP-1239, *Mortierella exigua* IFO 8571, *Mortierella hygrophila* IFO 5941, and *Mortierella elongata* IFO 8570, to obtain a cultured broth, wherein the culturing is carried out at a temperature between 10° C. and 20° C. for a sufficient period of time to produce a lipid containing eicosapentaenoic acid;
    separating said cultured broth to obtain microbial cells and a supernatant;
    extracting said microbial cells with an extraction agent to obtain an extract; and
    eliminating the extraction agent from the extract to recover the lipid containing eicosapentaenoic acid.

8. A process for producing a lipid containing eicosapentaenoic acid, comprising the steps of:
    culturing in a nutrient medium containing a microorganism selected from the group consisting of *Mortierella elongata* FERM BP-1239, *Mortierella exigua* IFO 8571, *Mortierella hygrophila* IFO 5941, and *Mortierella elongata* IFO 8570;
    adding to said medium during culturing an additive selected from the group consisting of a fatty acid, a salt of a fatty acid, and a lipid to obtain a cultured broth, wherein the culturing is carried out at a temperature between 10° C. and 20° C. for a sufficient period of time to produce a lipid containing eicosapentaenoic acid;
    separating said cultured broth to obtain microbial cells and a supernatant;
    extracting said microbial cells with an extraction agent to obtain an extract; and
    eliminating the extraction agent from the extract to recover the lipid containing the eicosapentaenoic acid.

* * * * *